(12) United States Patent
Breitenbach et al.

(10) Patent No.: US 6,497,886 B1
(45) Date of Patent: Dec. 24, 2002

(54) 1,3-BIS-(N-LACTAMYL) PROPANE AND THE PHARMACEUTICAL AND COSMETIC USE THEREOF

(75) Inventors: Jörg Breitenbach, Mannheim (DE); Siegfried Lang, Ludwigshafen (DE); Detlef Kratz, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,780

(22) PCT Filed: Oct. 7, 1997

(86) PCT No.: PCT/EP97/05499

§ 371 (c)(1),
(2), (4) Date: Apr. 1, 1999

(87) PCT Pub. No.: WO98/15291

PCT Pub. Date: Apr. 16, 1998

(30) Foreign Application Priority Data

Oct. 8, 1996 (DE) .......................... 196 41 437

(51) Int. Cl.$^7$ .......................... A61K 47/22; A61K 7/00; A61K 31/55; A61K 31/445; A61K 31/42
(52) U.S. Cl. .................. 424/401; 424/400; 514/212.08; 514/316; 514/376; 514/378; 514/424
(58) Field of Search .......................... 514/212.04, 230.8, 514/422, 183, 210.01, 315, 359, 418; 424/400, 401

(56) References Cited

U.S. PATENT DOCUMENTS

| | | | |
|---|---|---|---|
| 3,772,186 A | 11/1973 | Hort | 208/326 |
| 3,872,100 A | 3/1975 | Hort | 260/326 |
| 3,989,815 A | 11/1976 | Rajadhyaksha | 424/60 |
| 4,039,664 A | 8/1977 | Stoughton et al. | 424/180 |
| 5,120,735 A * | 6/1992 | Arika et al. | |
| 5,326,880 A | 7/1994 | Mandella et al. | 548/519 |
| 5,753,636 A | 5/1998 | Dornhofer et al. | 514/152 |

FOREIGN PATENT DOCUMENTS

| | | |
|---|---|---|
| EP | 271374 | 12/1986 |
| GB | 805026 | 11/1958 |

OTHER PUBLICATIONS

J. March, *Adv. Org. Chem.*, 3rd ed., 1985, pp. 377–379, and literature cited therein.

J. March, *Adv. Org. Chem.*, 3rd ed., 1985, pp. 709–710, and literature cited therein.

* cited by examiner

Primary Examiner—Russell Travers
Assistant Examiner—Alysia Berman
(74) Attorney, Agent, or Firm—Keil & Weinkauf

(57) ABSTRACT

The present invention relates to a 1,3-bis-(N-lactamyl) propane of general formula (I), wherein radicals $R^1$, $R^2$, $R^3$, $R^4$, $R^5$ and $R^6$ independently stand for hydrogen, alkyl, cycloalkyl, aryl or aralkyl and at least one of said radicals does not stand for hydrogen, (NLac) and (NLac') are the same or different and stand for N-lactamyl radicals. The invention also relates to the use of said substances as a solvent in pharmaceutical and cosmetic agents. Disclosed are novel compounds of formula (I), wherein $R^1$ and methyl and $R^2$–$R^6$ stand for hydrogen.

10 Claims, No Drawings

1,3-BIS-(N-LACTAMYL) PROPANE AND THE PHARMACEUTICAL AND COSMETIC USE THEREOF

This is a B71 of PCT/ECP97/05499 filed Oct. 7, 1997, which claims priority to German application No. 19641437.7, filed Oct. 8, 1996.

The present invention relates to 1,3-bis-(N-lactamyl) propanes and their use as solvents in pharmaceutical and cosmetic compositions.

A priority requirement in the development of an optimal administration form for a drug is that the bioavailability be good. As a rule, the most favorable conditions for this are provided by solutions of the active ingredient used, irrespective of whether a product for injection, a liquid oral drug form or, for example, a soft gelatin capsule preparation is concerned.

However, the solubility of many drugs in water is too low for them to be administered parenterally in the form of an aqueous solution, for example. Recourse is therefore frequently had to other solvents, for example organic, aqueous/organic or oily solvents.

It is important in the selection of suitable solvents to ensure that certain requirements are met. The solvent which is used must not be toxic, nor must it increase the toxicity of the active ingredient dissolved therein. It is, of course, necessary for the solvent to be compatible with the active ingredient, and it must not lead to inactivation or decomposition. Furthermore, the solvent must not induce irritation, sensitization or an allergic reaction either, and it should also be suitable for heat sterilization. For parenteral purposes, the viscosity should be low enough for injection with a relatively thin needle to be possible.

In addition, miscibility with other solvents, such as physiological saline or an infusion solution for preparing a product for injection or the oily vehicle in a soft gelatin capsule preparation, is important.

Besides water, well-known solvents are, for example, low molecular weight polyethylene glycols, 1,2-propylene glycol, ethanol, glycerol, benzyl alcohol, dimethylacetamide or neutral oils such as paraffin, castor oil or mixtures of triglycerides of saturated vegetable fatty acids.

However, the properties of the abovementioned solvents are not always satisfactory. Thus, the miscibility with other solvents may be limited, or the volume of solvents required to dissolve the active ingredient is so large that physiological tolerability is no longer ensured. For example, the widely used propylene glycol is immiscible with fixed oils. Benzyl alcohol has the disadvantage that its solubility in water is only 4%. Although glycerol is miscible with water, it is not soluble in fixed oils. In addition, the maximum glycerol concentration which can be used is limited to about 5% for tolerability reasons. Dimethyl-acetamide has very good dissolving properties but the tolerability is relatively poor so that use in humans does not appear acceptable.

The use of pyrrolidone derivatives such as 2-pyrrolidone, N-methylpyrrolidone and hydroxyethylpyrrolidone as solvents or cosolvents is known.

For example, EP-A 271 374 describes aqueous antibiotics compositions for veterinary use in which a tetracycline is dissolved in N-(hydroxyethyl)-2-pyrrolidone.

EP-A 626 171 discloses injection solutions for intravenous or intramuscular administration of oxytetracycline or doxycycline, the solvent phase being formed by N-methylpyrrolidone and/or 2-pyrrolidone.

A mixture of 2-pyrrolidone and N-methyl-2-pyrrolidone comprises the pharmaceutical vehicle of a composition for the cosmetic and therapeutic treatment of human beings and animals which is described in DE 26 15 140.

Although the formulations based on pyrrolidone derivatives described above have good solubility properties, they do not meet the strict requirements to be met by drugs, because the physiological tolerability is unsatisfactory. Furthermore, the absorption times are relatively long, and the serum levels achieved therewith are in need of improvement.

Nor do the bis- or poly-(N-pyrrolidonyl)alkanes described in the prior art sufficiently comply with the strict requirements to be met by pharmaceutical solvents. Thus, the asymmetric polypyrrolidonyl compounds of U.S. Pat. No. 3,989,815 are not at all intended for use as solvents; on the contrary they are used only as dispersants. The bis(N-pyrrolidonyl)alkanes described in U.S. Pat. No. 5,326,880 as vehicles for pharmaceutical compositions administered topically dissolve many active ingredients to only a limited extent. They are therefore unsuitable for pharmaceutical preparations where good solubility of the active ingredient matters.

It is an object of the present invention to provide solvents for pharmaceutical preparations which, besides an excellent dissolving capacity for the active ingredient used, also provide excellent miscibility with other solvents and good physiological tolerability.

We have found that this object is achieved by certain, asymmetric 1,3-bis-(N-lactamyl)propanes which are excellent solvents for a large number of active ingredients of low solubility in water and, furthermore, can be used universally because they are miscible in any ratio with other conventional pharmaceutical solvents. The compounds according to the invention are chemically inert and show high physiological tolerability.

The present invention relates to the use of at least one 1,3-bis(N-lactamyl)propane of the formula I

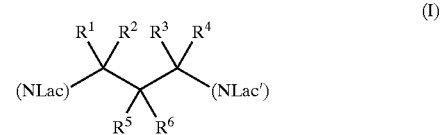

where $R^1$, $R^2$, $R^3$, $R^4$, $R^5$ and $R^6$ are, independently of one another, hydrogen, alkyl, cycloalkyl, aryl or aralkyl, and at least one of these radicals is not hydrogen, (NLac) and (NLac') are identical or different and are N-lactamyl radicals, as solvents in pharmaceutical or cosmetic compositions.

The term "alkyl" comprises straight-chain or branched alkyl groups, preferably $C_1$–$C_{10}$-alkyl, in particular $C_1$–$C_6$-alkyl and, particularly preferably, $C_1$–$C_3$-alkyl, such as methyl, ethyl, n- and i-propyl, n-, i- or t-butyl, n-pentyl, neopentyl or n-hexyl, etc.

"Cycloalkyl" comprises cyclic alkyl groups such as cyclopropyl, cyclobutyl, cyclopentyl, cyclohexyl, cycloheptyl, cyclooctyl and polycyclic radicals such as norbornyl, camphyl, pinanyl or decahydronaphthyl, it being possible for both the mono- and the polycyclic radicals to be substituted by one or more $C_1$–$C_4$-alkyl groups.

The term "aryl" comprises aromatic radicals, preferably naphthyl and, in particular, phenyl.

"Aralkyl" means aryl groups which are connected via a $C_1$–$C_4$-alkylene unit to the basic framework. "Aralkyl" is preferably benzyl.

"Alkylene" means linear or branched divalent alkyl radicals, preferably $C_1$–$C_6$-alkylene and, in particular, $C_1$–$C_4$-alkylene, such as methylene, 1,1- and 1,2-ethylene, 1,1-, 1,2-, 1,3- and 2,2-propylene, 2-methyl-1,1-propylene etc.

The term "N-lactamyl" represents N-substituted mono- or polycyclic lactams which may be substituted by $C_1$–$C_4$-alkyl groups, $C_1$–$C_4$-alkoxy groups or halogen, and/or be fused to aromatic systems, and/or contain further hetero atoms, preferably nitrogen or oxygen, in the lactam ring. Particularly preferred N-lactamyl radicals are derived from pyrrolidone, piperidone, δ- or ε-caproactam, 4-oxazolidinone or tetrahydro-1,4-oxazin-3-one and, in particular, from pyrrolidone.

In 1,3-bis-(N-lactamyl)-propanes according to the invention which are preferably used as solvents in pharmaceutical compositions, at least one of the radicals $R^1$, $R^2$, $R^3$, $R^4$, $R^5$ and $R^6$ is alkyl, while the remainder of these radicals are hydrogen.

Particularly suitable compounds of the formula I are those where only one of $R^1$, $R^2$, $R^3$, $R^4$, $R^5$ and $R^6$ is not hydrogen, with $R^1$ being preferred in this case and being, in particular, alkyl.

In a particular embodiment, 1,3-bis-(N-lactamyl)butanes are used, i.e. compounds of the formula I where $R^1$ is methyl.

The lactamyl groups (NLac) and (NLac') in formula I may be identical or different, but they are preferably identical.

A particular class of compounds for use as solvents in pharmaceutical preparations are those compounds of the type described above which have no center of symmetry. Compounds of this type result when the substituted propylene unit is asymmetric per se and/or the lactamyl radicals NLac and NLac' are different. Preferred compounds are those where the propylene unit is asymmetric and the two lactamyl radicals have the same meaning.

The following compounds are very particularly preferred:
1,3-Bis(1-pyrrolidonyl)butane
1,3-Bis(1-piperidonyl)butane
1,3-Bis(1-caprolactamyl)butane
1,3-Bis(tetrahydro-1,4-oxazin-3-on-1-yl)butane
1,3-Bis(oxazolidin-4-on-3-yl)butane
1-(1-Caprolactamyl)-3-(1-piperidonyl)butane
3-(1-Caprolactamyl)-1-(1-piperidonyl)butane
1-(1-Caprolactamyl)-3-(1-pyrrolidonyl)butane
3-(1-Caprolactamyl)-1-(1-pyrrolidonyl)butane
1-(1-Caprolactamyl)-3-(oxazolidin-4-on-3-yl)butane
3-(1-Caprolactamyl)-1-(oxazolidin-4-on-3-yl)butane
1-(1-Caprolactamyl)-3-(tetrahydro-1,4-oxazin-3-on-4-yl)butane
3-(1-Caprolactamyl)-1-(tetrahydro-1,4-oxazin-3-on-4-yl)butane
1-(Oxazolidin-4-on-3-yl)-3-(1-piperidonyl)butane
3-(Oxazolidin-4-on-3-yl)-1-(1-piperidonyl)butane
1-(Oxazolidin-4-on-3-yl)-3-(1-pyrrolidonyl)butane
3-(Oxazolidin-4-on-3-yl)-1-(1-pyrrolidonyl)butane
1-(Oxazolidin-4-on-3-yl)-3-(tetrahydro-1,4-oxazin-3-on-4-yl)-butane
3-(Oxazolidin-4-on-3-yl)-1-(tetrahydro-1,4-oxazin-3-on-4-yl)-butane
1-(1-Piperidonyl)-3-(1-pyrrolidonyl)butane
3-(1-Piperidonyl)-1-(1-pyrrolidonyl)butane
1-(1-Piperidonyl)-3-(tetrahydro-1,4-oxazin-3-on-4-yl)butane
3-(1-Piperidonyl)-1-(tetrahydro-1,4-oxazin-3-on-4-yl)butane
1-(1-Pyrrolidonyl)-3-(tetrahydro-1,4-oxazin-3-on-4-yl)butane
3-(1-Pyrrolidonyl)-1-(tetrahydro-1,4-oxazin-3-on-4-yl)butane.

Some of the compounds which are suitable according to the invention and are described above have one or more asymmetric carbon atoms and may therefore exist in different stereochemical forms. This invention relates both to the individual isomers (enantiomers or diastereomers) and to mixtures thereof.

The preparation of compounds of the formula I is known in principle. Thus, Breitenbach et al. (Naturwissenschaften 42, 1955, 155; 440) describe the dimerization of N-vinylpyrrolidone under acidic reaction conditions and subsequent hydrogenation of the resulting 1,3-bis-(N-pyrrolidonyl)-1-butene to 1,3-bis -(N-pyrrolidonyl)butane. Based on this procedure, it is possible as shown in scheme I to prepare, by acid-catalyzed reaction of the vinyllactams of the formula Ia or IIb, where $R_a$, $R_b$, $R_c$ and $R_d$ are, independently of one another, hydrogen, alkyl, cycloalkyl, aryl or aralkyl, and (NLac) and (NLac') are the abovementioned lactamyl radicals, the propenes of the formula IIIa–d. The compounds III a–d are subsequently converted by hydrogenation into the corresponding compounds of the formula I a–d. The compounds I a–d correspond to those compounds of the formula I in which two radicals on adjacent carbon atoms, for example $R^1$ and $R^5$, are hydrogen. When mixtures of two vinyllactams of the formula II are used, it is possible to obtain both the mixed reaction products and the two products of a reaction of the vinyllactams II with themselves. The compounds can be separated both at the stage of the propenes IIIa–d and at the stage of the final products Ia–d, but this is not always necessary for preparing the solvents according to the invention. Preferably prepared in this way are the compounds I obtained by reaction of the vinyllactams IIa and IIb with themselves (Ia and Id respectively).

Scheme I

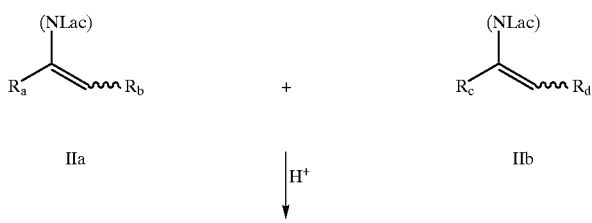

-continued

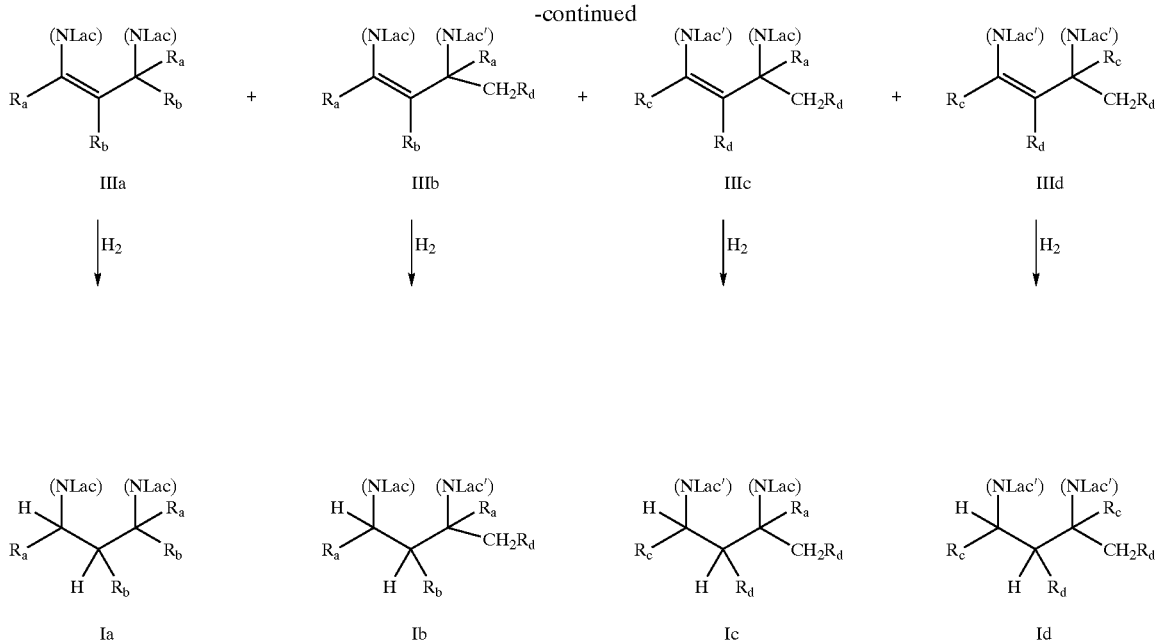

The vinyllactams of the formula Ia or IIb which are employed are known or can be prepared by general processes based on the preparation of the known vinyllactams II. There are no restrictions on the configuration of the olefinic double bonds in the compound of the formula II.

The vinyllactams II can be converted into the bis-(N-lactamyl)-propenes III by conventional methods of acid-catalyzed dimerization of olefins using a protic acid, a Lewis acid catalyst or Ziegler catalysts (see, for example, J. March, Advanced Organic Chemistry $3^{rd}$ ed., page 709 and literature cited therein). The reaction can take place either without diluent or else in an inert solvent, eg. a halogenated hydrocarbon such as $CH_2Cl_2$, aromatic compounds such as toluene, ethers such as diethyl ether, dioxane or tetrahydrofuran, or another solvent which is suitable for electrophilic reactions. Preferred catalysts are strong protic acids, preferably those with corresponding anions of low nucleophilicity, such as sulfuric acid, sulfonic acids, eg. p-toluenesulfonic acid, methanesulfonic acid or trifluoromethanesulfonic acid, perchloric acid or hydrogen chloride. The acid is preferably employed in substoichiometric amount based on the vinyllactams, in particular in catalytic amount and, particularly preferably in amounts of up to 5 mol %. The reaction is preferably carried out at temperatures in the range from −20° to +60° C. and, in particular, in the range from 10° to 40° C.

The subsequent hydrogenation step can take place by the conventional processes for hydrogenating olefinic double bonds (see J. March, Advanced organic Chemistry, 3rd ed., pages 691–708 and literature cited therein), preferably by catalytic hydrogenation with hydrogen on transition metal catalysts. Because of their enamine characteristics, the double bonds in the propene moiety of III display high reactivity which permits this double bond to be hydrogenated selectively in the presence of other, less reactive double bonds.

Another route to 1,3-bis-(N-lactamyl)propanes consists of reacting 1,3-diamines of the formula IV, where $R^1$, $R^2$, $R^3$, $R^4$, $R^5$ and $R^6$ have the meanings stated above for I, with suitable lactones (see scheme II; OLac is the lactone corresponding to the relevant N-lactamyl radical (N-Lac)).

Scheme II

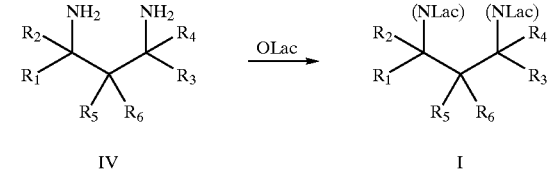

U.S. Pat. No. 5,326,880 describes this procedure for the example of the preparation of 1,3-bis-(N-pyrrolidonyl) pentane. The procedure indicated therein can be applied to the preparation of the compounds of the formula I according to the invention.

Another possibility for preparing compounds of the formula I starts from 1,3-functionalized compounds of the formula V where X and Y, which can be identical or different, are suitable leaving groups, eg. halide, tosylate, brosylate or trifluoromethane-sulfonate, and $R^1$, $R^2$, $R^3$, $R^4$, $R^5$ and $R^6$ have the abovementioned meanings. Compounds of this type are reacted with suitable N-lactamyl anions to give the 1,3-bis-(N-lactamyl)propanes of the formula I (scheme III). The particular lactamyl anions (NLac)⁻ are obtainable as a rule by treating the lactams (N-NLac) with suitable bases such as alkali metal or alkaline earth metal hydroxides, alcoholates, alkali metal hydrides or amides. The reaction of the compounds V with the anions of the lactams can be carried out by conventional methods for N-alkylation of amides (cf. J. March, Advanced organic Chemistry, $3^{rd}$ ed., pages 377 et seq. and literature cited therein). It is moreover possible for the 1,3-difunctionalized compounds V to be reacted either with the lactams in the presence of a base or else with the anions of the lactams which have been previously generated. If X and Y differ in reactivity, it is possible, especially in the latter case, to obtain compounds of the formula I with different lactamyl radicals.

Scheme III

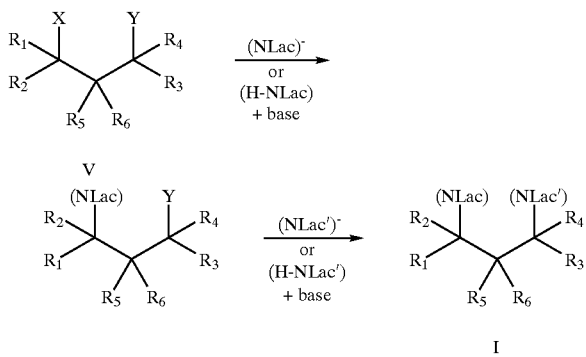

Suitable 1,3-difunctionalized compounds are starting materials frequently employed in organic synthesis and can be obtained, for example, starting from aldoles by modification of the functional groups by known processes or starting from cyclopropanes by halo-genating cleavage of the cyclopropane unit.

The present invention also relates to 1,3-bis(N-lactamyl) propanes of the formula Ia

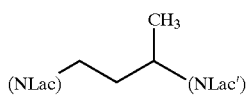

where (NLac) and (NLac') identical or different and are N-lactamyl radicals.

The N-lactamyl radicals in the abovementioned compounds are preferably derived from, in particular, unsubstituted pyrrolidones, piperidones, δ- or ε-caprolactam, tetrahydro-1,4-oxazin-3-ones or 4-oxazolidinones. Pyrrolidone, piperidone or ε-caprolactam particularly preferred. (NLac) and NLac') preferably have the same meaning.

The N-lactamyl radicals preferably represent pyrrolidone. However, interesting compounds are also produced if at least one of the, and in particular both, N-lactamyl radicals, which may be identical or different, have a ring with at least 6 members.

The use according to the invention of the 1,3-bis-(N-lactamyl)-propanes of the formula I as solvents extends to all pharmaceutical preparations which are known to the skilled worker and in which the active ingredient(s) is (or are) used in dissolved form. Formulations of these types can be administered orally, ophthalmologically, rectally, parenterally, (for example by the intravenous, intramuscular, subcutaneous, intradermal, intraperitoneal, intrathoracic, intraarterial, intracardiac, intraspinal, intrasynovial-routes etc.), intraarticularly, topically, nasally or buccally. Suitable presentations comprise capsules, for example soft gelatin capsules, embrocations, lotions, applications, creams, ointments, gels, drops, self-propellant formulations and spray formulations.

The compounds according to the invention are particularly employed for preparing pharmaceutical compositions for systemic and, in particular, parenteral, and topical use. The compounds of the formula I are particularly suitable as solvents for injectable products, for example preparations for injection and infusion, and in the contents of capsules, for example soft gelatin capsules. Parenteral preparations which contain the compounds according to the invention in combination with polyvinylpyrrolidones have proven particularly advantageous. The polyvinylpyrrolidone content is preferably in the range from 1 to 70%, preferably 5 to 60%, of the total weight of the combination. It is possible on use of a combination of this type to produce parenteral preparations, in particular injectable products, with a long-lasting action.

In topical products, the compounds according to the invention are able to increase the rate of absorption of active ingredients.

The present invention also relates to pharmaceutical compositions which contain at least one 1,3-bis(N-lactamyl) propane of the formula I. Besides these compounds according to the invention, the pharmaceutical composition contains at least one active ingredient with or without other conventional vehicles and/or ancillary substances.

The amount of active ingredient per dose unit and the concentration may vary within wide limits. The only condition is that they suffice to achieve the desired effect. It is also possible to employ combinations of active ingredients. Active ingredients for the purpose of the invention include vitamins and minerals, an d crop treatment agents and insecticides. Active ingredients for the purpose of the invention also include therapeutic peptides. Hydrophilic active ingredients are particularly suitable.

The solvents according to the invention can be used to dissolve the following active ingredients, for example:

Acebutolol, acetylcysteine, acetylsalicylic acid, acyclovir, alprazolam, alfacalcidol, allantoin, allopurinol, ambroxol, ambkacin, amiloride, aminoacetic acid, amiodarone, amitriptyline, amlodipine, amoxicillin, ampicillin, ascorbic acid, aspartame astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, choramphenicol, chlorhexidine, chlorpheniramine, chlortalidone, choline, cyclosporin, cilastatin, cimetidine, ciprofloxacin, cisapride, cisplatin, clarithromycin, clavulan acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiolms etoposide, Eucalyptus globulus, famotidine, felodipine, fenofibrate, fenoterol, fentanyl, flavin-mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide-dinitrate, isosorbide mononitrate, isotretinoin, ketotifen, ketoconazole, ketoprofen, ketorolac, labetalol, lactulose, lecithin, levocarnitine, levodopa, levoglutamid, levonorgestrel, levothyroxine, lidocaine, lipase, imipramine, lisinopril, loperamide, lorazepam, lovastatin, medroxy-progesterone, menthol, methotrexate, methyldopa, methyl-prednisolone, metoclopramide, metoprolol, miconazole, midazolam, minocycline, minoxidil, misoprostol, morphine, multivitamin mixtures and combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazile, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatotropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are those which can be dissolved in particularly high concentration in the solvents according to the invention. These include acetylcysteine, acetylsalicylic acid, anipamilxHCl, phenylbutazone, captopril, esuprone, flecainide, nexopamil, nitrofurantoin, (+)-pseudoephedrinexHCl, seleginexHCl, hydantoins such as 5,5-diphenylhydantoin, benzodiazepines such as diazepam, chlordiazepoxide, pyrazolone derivatives such as diphenylbutazone, aminophenazone, dimethyl-aminophenazone, carbamates such as meprobamate, barbiturates such as phenobarbital, pentobarbital, aminobarbital, antibiotics such as amoxicillin, ciprofloxacin, chloramphenicol, oxytetracyclines, virustatics such as acyclovir, famcyclovir, and antimycotics such as ketoconazole, fluconazole and itraconazole, sulfonamides such as sulfamethoxazole, sulfamoxole, sulfathiazine, steroids such as prednisolone, cyproterone acetate, hydroxyprogesteronecaproate, sulfonamide potentiators such as trimethoprim, non-steroidal antirheumatics (NSAR) such as ibuprofen, diclofenac, mefenamic acid or theophylline. The fat-soluble vitamins A, E, K and their derivatives, such as vitamin A palmitate, acetate or propionate, vitamin E acetate or nicotinate, can be mixed in any ratio with the compounds according to the invention; the same applies to vitamin C. The lower viscosity is also advantageous, which often has a disadvantageous effect on use of oils or semi-synthetic fatty acid esters. Also suitable are the β-blocker class, Ca antagonists, ACE inhibitors, α-blockers, H2 antagonists, lipid lowering agents, antihistamines, antiepilectics and NS psychopharmaceuticals.

Particular suitable are benzocaine, chloramphenicol, cyclosporin, clotrimazole, 5,5-diphenylhydantoin, fenofibrate, furosemide, is gallopamilxHCl, glibenclamide, hydrochlorothiazide, ketoprofen, ibuprofen, indometacin, naftidrofuryl, nifedipine, nitrendipine,. omeprazole, paracetamol, pentoxifylline, prazosin, propafenonexHCl, sulfamethazine, sulfamethoxazole, sulfathiazole, sulindac, tolbutamide, tramadol and zotepine.

The choice of suitable vehicles and ancillary substances depends on the nature of the active ingredient and, in particular, of the formulations.

Examples of conventional vehicles or ancillary substances which are suitable for the purposes of the present invention are solvents which are miscible with the solvents according to the invention, such as water, ethanol, glycerol, 1,2-propylene glycol, low molecular weight polyethylene glycols, tetraglycol, dimethylacetamide, dimethylformamide, benzyl alcohol, neutral oils such as paraffin, olive oil, sesame oil, arachis oil, castor oil or mixtures of triclycerides of saturated vegetable fatty acids;

salts to adjust the tonicity in order preferably to obtain isotonic solutions;

buffers to adjust the pH in order to obtain, in particular, formulations with the physiological pH;

agents to increase the viscosity, eg. on topical use, such as polyethylene glycols, polyvinylpyrrolidone or polyacrylates and cellulose ethers;

stabilizers such as antioxidants to protect medicinal substances which are sensitive to oxidation, for example sulfite, sodium sulfoxylate, cysteine, ascorbic acid, α-tocopherol or else compounds which complex heavy metal ions, such as EDTA disodium salts;

preservatives such as antimicrobial agents in bacteriostatic or fungistatic concentrations, for example phenylmercuric nitrate, thiomersal, benzethonium chloride, benzalkonium chloride, phenol, cresol or chlorobutanol;

masking flavors which are used, in particular, for oral preparations;

and other vehicles and ancillary substances which can conventionally be used for formulating the drugs according to the invention.

The cosmetic compositions are in the form of, in particular, creams, gels, ointments or solutions. The cosmetic compositions are formulated in a conventional way, for example as indicated above for topical pharmaceutical compositions.

The following examples describe the invention without restricting it:

Preparation of bis-(N-lactamyl)Butanes

EXAMPLES 1 to 4

Example 1

1,3-Bis-(1-pyrrolidonyl)Butene

A stream of HCl gas was passed through a capillary into 25 g of N-vinylpyrrolidone, which had been purified by crystallization, under nitrogen for 10 sec. The mixture was stored at 0° C. under a nitrogen atmosphere overnight, during which slow crystallization started. 10 ml of ether were added to complete the crystallization. 1,3-Bis-(1-pyrrolidonyl)butene crystallized in clusters of needles. The product was recrystallized from ether/acetone (1/5).

Melting point: 72° C. Yield: 78% $^{13}$C-NMR (MHz, CDCl$_3$):δ=174.01, 173.17, 125.14, 110.58, 46.08, 45.17, 42.31, 31.44, 31.15, 17.92, 17.39, 17.29 ppm.

Example 2

1,3-Bis-(1-pyrrolidonyl)Butane 60 g of 1,3-bis-(1-pyrrolidonyl)butene, 1000 ml of glacial acetic acid and 10 g of 10% palladium on carbon were mixed under inert gas. Subsequently, hydrogen was passed in while stirring at room temperature. The hydrogen uptake was complete after about 30 min. Reaction was allowed to continue at room temperature for a further 90 min. The catalyst was filtered off and the filtrate was concentrated under reduced pressure. The oily crude product was subsequently distilled under reduced pressure.

Boiling point: 205–215° C. (0.2 mbar) Yield: 90% $^{13}$C-NMR (MHz, CDCl$_3$):δ=174.58, 174.42, 47.16, 44.29, 41.87, 39.59, 31.45, 31.32, 30.91, 18.08, 17.94, 17.92 ppm. MS (CI): m/z =224 (M$^+$, 70), 196 (60), 126 (100), 113 (95), 98 (50). IR (Film): ν [cm$^{-1}$]=2995 (CH,s), 1680 (CO,s), 1425, 1286.

Example 3

1,3-Bis-(1-caprolactamyl)Butene

Preparation took place starting from 25 g of N-vinylcaprolactam, which had been purified by distillation, by the method of Example 1

Melting point: 178° C. Yield: 76% $^{13}$C-NMR (MHz, CDCl$_3$):δ=174.97, 173.98, 128.15, 110.02, 48.39, 45.14, 43.04, 37.56, 37.06, 29.93, 29.65, 29.25, 27.53, 23.46, 23.41, 17.13 ppm.

Example 4

1,3-Bis-(1-caprolactamyl)Butane 1,3-Bis-(1-caprolactamyl)butane was prepared starting from 60 g of 1,3-bis-(1-caprolactamyl)butene as in Example 2.

Tests of the Solubility in 1,3-bis(N-lactamyl) Butanes

EXAMPLES 5 and 6

Example 5

1,3-Bis(N-lactamyl)Butanes as Solvent

To 20 ml 1,3-bis(1-pyrrolidonyl)butane was added the active ingredient in an amount which is above the amount of this active ingredient able to dissolve in this volume. It was stirred at room temperature for 72 hours. As a rule, this time ensured that the saturation solubility in the medium was reached. After subsequent filtration, the content of active ingredient in the filtrate was determined by UV photometry. The indicated solubilities were found for the following active ingredients:

| Active ingredient | maximum solubility at 22° C. |
| --- | --- |
| Prednisone | 200 mg/ml |
| Sulfathiazole | 200 mg/ml |
| Trimethoprim | 150 mg/ml |
| Esuprone | 190 mg/ml |
| Paracetamol | 250 mg/ml. |

Example 6

1,3-Bis(N-lactamyl)Butanes as Cosolvent Mixed with Water

The method used to determine the maximum soluble amount of active ingredient was as in Example 5. The following solutions were tested:

a) 1,3-Bis(1-pyrrolidonyl)butane (DHVP):water (1:1)
b) 1,3-Bis(1-pyrrolidonyl)butane (DHVP):water (1:3)
c) 1,3-Bis(1-caprolactamyl)butane (DHVC):water (1:1)
d) 1,3-Bis(1-caprolactamyl)butane (DHVC):water (1:3)
e) 1,2-Propylene glycol (1,2-PG):water (1:1)
f) 1,2-Propylene glycol (1,2-PG):water (1:3)
g) Phosphate buffer pH 7.0.

The results for the active ingredient trimethoprim (E 1%: 209.948 ml/g at 288 nm in methanol/water 1:1) were as follows:

| Solution (20 ml) | weight [g] | pH | Extinction | Dilution | Dissolved substance [g] | Solubility [%] |
| --- | --- | --- | --- | --- | --- | --- |
| 50% 1,2-PG | 0.3394 g | 8.05 | 0.62457 | 300 | 0.1785 | 0.89 |
| 25% 1,2-PG | 0.3410 g | 7.54 | 0.58575 | 100 | 0.0558 | 0.28 |
| 50% DHVP | 0.8113 g | 8.61 | 0.74501 | 1000 | 0.7097 | 3.55 |
| 25% DHVP | 0.4126 g | 7.44 | 0.21658 | 1000 | 0.2063 | 1.03 |
| 50% DHVC | 1.7779 g | 8.45 | 1.06760 | 1000 | 1.0170 | 5.09 |
| 25% DHVC | 0.3892 g | 7.72 | 0.35504 | 1000 | 0.3382 | 1.69 |
| Phosphate buffer pH 7.0 | 0.3712 g | 7.19 | 0.25705 | 100 | 0.0245 | 0.12 |

The results for the active ingredient theophylline (E 1%: 549.4755 ml/g at 272 nm in methanol/water 1:1) were as follows:

| Solution (20 ml) | Weight [g] | pH | Extinction | Dilution | Dissolved substance [g] | Solubility [%] |
| --- | --- | --- | --- | --- | --- | --- |
| 50% 1,2-PG | 0.9607 | 7.53 | 0.84715 | 1000 | 0.3083 | 1.54 |
| 25% 1,2-PG | 0.9991 | 7.34 | 0.54880 | 1000 | 0.1998 | 1.00 |
| 50% DHVP | 1.0473 | 7.75 | 1.01740 | 1000 | 0.3703 | 1.85 |
| 25% DHVP | 0.9924 | 7.35 | 0.71689 | 1000 | 0.2609 | 1.30 |
| 50% DHVC | 1.0307 | 7.53 | 0.50153 | 3000 | 0.5476 | 2.74 |
| 25% DHVC | 1.0472 | 7.23 | 0.85304 | 1000 | 0.3105 | 1.55 |
| Phosphate buffer pH 7.0 | 1.0014 | 7.09 | 0.32199 | 1000 | 0.1172 | 0.59 |

The results for the active ingredient paracetamol (E 1%: 756.2982 ml/g at 246 nm in methanol/water 1:1) were as follows:

| Solution (20 ml) | Weight [g] | pH | Extinction | Dilution | Dissolved substance [g] | Solubility [%] |
| --- | --- | --- | --- | --- | --- | --- |
| 50% 1,2-PG | 2.7846 | 7.72 | 0.48834 | 10000 | 1.2914 | 6.46 |
| 25% 1,2-PG | 0.9787 | 7.42 | 0.69788 | 3000 | 0.5537 | 2.77 |
| 50% DHVP | 8.2911 | 7.81 | 0.63400 | 30000 | 5.0298 | 25.15 |
| 25% DHVP | 2.8011 | 7.42 | 0.80333 | 10000 | 2.1244 | 10.62 |
| Phosphate buffer pH 7.0 | 1.0312 | 7.09 | 1.02790 | 1000 | 0.2718 | 1.36 |

The solubilities which were found show that 1,3-bis-(1-pyrrolidonyl)butane and 1,3-bis-(1-caprolactamyl)butane are better cosolvents mixed with water for hydrophilic active ingredients, such as paracetamol, theophylline or trimethoprim, than the widely used propylene glycol.

Example 7

Comparison of the Solubility in 1,3-bis-(1-pyrrolidonyl)Butane (DHVP) and 1,3-bis-(1-pyrrolidonyl)Propane 30% by weight of the following active ingredients were dissolved in 1,3-bis-(1-pyrrolidonyl)butane (DHVP):

acetylcysteine, acetylsalicylic acid, anipamil×HCl, benzocaine, benzolidin, captopril, chloramphenicol, clotrimazole, 5,5-diphenylhydantoin, fenofibrate, flecainide, furosemide, gallopamil×HCl, glibenclamide, hydrochlorothiazide, ibuprofen, indometacin, naftidrofuryl, nexopamil, nifedipine, nitren-dipine, nitrofurantoin, paracetamol, (+)-pseudoephedrine×HCl, pentoxifylline, prazosin, propafenone×HCl, selegiline×HCl, sulfamethazine, sulfamethoxazole, sulfathiazole, sulindac and tolbutamide.

However, on use of 1,3-bis-(1-pyrrolidonyl)propane, which is known in the prior art, in place of the 1,3-bis-(1-pyrrolidonyl)-butane according to the invention, under conditions which were otherwise the same, the following active ingredients recrystallized, i.e. it was impossible with 1,3-bis-(1-pyrrolidonyl)propane to obtain stable 30-% solutions of these active ingredients:

benzocaine, chloramphenicol, cyclosporin, clotrimazole, 5,5-diphenylhydantoin, fenofibrate, furosemide, gallopamil×HCl, glibenclamide, hydrochlorothiazide, indometacin, naftidrofuryl, nifedipine, nitrendipine, paracetamol, pentoxifylline, prazosin, propafenone×HCl, sulfamethazine, sulfamethoxazole, sulfathiazole, sulindac and tolbutamide.

Pharmaceutical and Cosmetic Formulations

EXAMPLES 8 to 121

Example 8

Preparation of an Oxytetracycline Injection Solution

| Oxytetracycline | 22.65 g |
|---|---|
| Magnesium oxide | 1.92 g |
| 1,3-Bis-(1-pyrrolidonyl)butane | 40.00 g |
| Polyvinylpyrrolidone K 17 (eg. Kollidon 17 PF) | 5.00 g |
| Magnesium formaldehyde sulfoxylate | 0.44 g |
| 2-Aminoethanol | 3.84 g |
| Water ad | 100.00 ml |

Water and 1,3-bis-(1-pyrrolidon)butane are mixed, and Kollidon 17 PF is dissolved therein; the solution is heated to 75° C. and magnesium formaldehyde sulfoxylate is added and dissolved with stirring. After the magnesium oxide has been suspended, oxytetracycline is slowly stirred in until a clear solution results. After cooling, the pH is adjusted to 8.5 with aminoethanol.

Example 9

Preparation of a Trimethoprim/sulfonamide Combination as Injection Solution

| Trimethoprim | 2.0 g |
|---|---|
| Sulfadoxine | 10.0 g |
| 1,3-Bis-(1-pyrrolidonyl)butane | 56.0 g |
| Water | 29.0 g |
| Sodium hydroxide solution ad | (pH 8.5) |

The two active ingredients are dissolved in 1,3-bis(1-pyrrolidonyl)butane, the water is added, and the pH is adjusted to 8.5 with sodium hydroxide solution.

Example 10

Sulfamoxole/trimethoprim Injection Solution

| Sulfamoxole | 4.0 g |
|---|---|
| Trimethoprim | 0.8 g |
| 1,3-Bis-(1-pyrrolidonyl)butane | 30.0 g |
| Sodium sulfite | 0.4 g |
| Ethanol | 10.0 g |
| 1,2-Propylene glycol | 10.0 g |
| p-Hydroxybenzoate | 0.2 g |
| Water for injection ad | 100.0 ml |

Example 11

Gel Preparation

| Ibuprofen | 10.0 g |
|---|---|
| 1,3-Bis-(1-pyrrolidonyl)butane | 20.0 g |
| Lutrol F 127 (polyethylene glycol) | 22.0 g |
| Lutrol F 68 (polyethylene glycol) | 5.0 g |
| NaCl | 1.0 g |
| Water | 51.0 g |

Properties: clear, colorless gel

Example 12

Oil-in-water Cream Formulas

Skin care cream

| Liquid paraffin | 24.0 g |
|---|---|
| Cremophor S9 (PEG-9 stearate) | 5.0 g |
| Beeswax | 6.0 g |
| Cutina ®CP (cetyl palmitate) | 2.0 g |
| 1,3-Bis-(1-pyrrolidonyl) butane | 3.0 g |
| Water | 60.0 g |

Moisturizer cream with collagen

| Cremophor S9 (PEG-9 stearate) | 7.0 g |
|---|---|
| 1,3-Bis-(1-pyrrolidonyl)butane | 1.5 g |
| Cetyl alcohol | 6.0 g |
| Wool wax | 3.0 g |
| Tegiloxan ®350 (dimethicone) | 2.0 g |
| Miglyol 812 (caprylic/capric acid | 5.0 g |

-continued

| triglyceride) | |
|---|---|
| Karion ® F (sorbitol) | 3.0 g |
| Collagen | 5.0 g |
| (−)alpha-Bisabolol | 0.1 g |
| Preservative | q.s. |
| Perfume oil | q.s. |
| Water | 67.4 g |

It is possible to introduce active ingredients or vitamins into these formulations.

We claim:

1. A pharmaceutical or cosmetic composition comprising at least one 1,3-bis(N-lactamyl)butane of the formula Ia

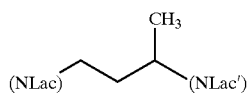

where (NLac) and (NLac') are identical or different and are N-lactamyl radicals,
and at least one pharmaceutically or cosmetically active ingredient.

2. The composition of claim 1, wherein (NLac) and (NLac'), which can be identical or different, are selected from pyrrolidone, piperidone, δ- or ε-ca-prolactam, tetrahydro-1,4-oxazin-3-one and 4-oxazolidinone.

3. The composition of claim 1, wherein (NLac) and (NLac') have the same meaning.

4. The composition of claim 1, comprising a compound which is selected from 1,3-Bis(1-pyrrolidonyl)butane
1,3-Bis(1-piperidonyl)butane
1,3-Bis(1-caprolactamyl)butane
1,3-Bis(tetrahydro-1,4-oxazin-3-on-1-yl)butane
1,3-Bis(oxazolidin-4-on-3-yl)butane
1-(1-caprolactamyl)-3-(1-piperidonyl)butane
3-(1-caprolactamyl)-1-(1-piperidonyl)butane
1-(1-caprolactamyl)-3-(1-pyrrolidonyl)butane
3-(1-caprolactamyl)-1-(1-pyrrolidonyl)butane
1-(1-caprolactamyl)-3-(oxazolidin-4-on-3-yl)butane
3-(1-caprolactamyl)-1-(oxazolidin-4-on-3-yl)butane
1-(1-caprolactamyl)-3-(tetrahydro-1,4-oxazin-3-on-1-yl)butane
3-(1-caprolactamyl)-1-(tetrahydro-1,4-oxazin-3-on-1-yl)butane
1-(oxazolidin-4-on-3-yl)-3-(1-piperidonyl)butane
3-(oxazolidin-4-on-3-yl)-1-(1-piperidonyl)butane
1-(oxazolidin-4-on-3-yl)-3-(1-pyrrolidonyl)butane
3-(oxazolidin-4-on-3-yl)-1-(1-pyrrolidonyl)butane
1-(oxazolidin-4-on-3-yl)-3-(tetrahydro-1,4-oxazin-3-on-1-yl)butane
3-(oxazolidin-4-on-3-yl)-1-(tetrahydro-1,4-oxazin-3-on-1-yl)butane
1-(1-piperidonyl)-3-(1-pyrrolidonyl)butane
3-(1-piperidonyl)-1-(1-pyrrolidonyl)butane
1-(1-piperidonyl)-3-(tetrahydro-1,4-oxazin-3-on-1-yl)butane
3-(1-piperidonyl)-1-(tetrahydro-1,4-oxazin-3-on-1-yl)butane
1-(1-pyrrolidonyl)-3-(tetrahydro-1,4-oxazin-3-on-1-yl)butane
3-(1-pyrrolidonyl)-1-(tetrahydro-1,4-oxazin-3-on-1-yl)butane.

5. A 1,3-bis(N-lactamyl)butane of the formula Ia

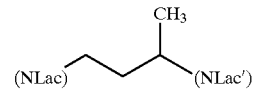

where (NLac) and (NLac') are identical or different and are N-lactamyl radicals; except for 1,3-bis(1-pyrrolidonyl)butane.

6. A compound as claimed in claim 5, of the formula Ia, where (NLac) and (NLac'), which can be identical or different, are N-lactamyl radicals which are selected from pyrrolidone, piperidone, δ- or ε-caprolactam, tetrahydro-1,4-oxazin-3-one or 4-oxazolidinone.

7. A compound as claimed in claim 5, of the formula Ia, where (NLac) and (NLac') have the same meaning.

8. A compound as claimed in claim 5, which is selected from the group consisting of 1,3-Bis(1-piperidonyl)butane,
1,3-Bis(1-caprolactamyl)butane,
1,3-Bis(tetrahydro-1,4-oxazin-3-on-1-yl)butane,
1,3-Bis(oxazolidin-4-on-3-yl)butane,
1-(1-caprolactamyl)-3-(1-piperidonyl)butane,
3-(1-caprolactamyl)-1-(1-piperidonyl)butane,
1-(1-caprolactamyl)-3-(1-pyrrolidonyl)butane,
3-(1-caprolactamyl)-1-(1-pyrrolidonyl)butane,
1-(1-caprolactamyl)-3-(oxazolidin-4-on-3-yl)butane,
3-(1-caprolactamyl)-1-(oxazolidin-4-on-3-yl)butane,
1-(1-caprolactamyl)-3-(tetrahydro-1,4-oxazin-3-on-1-yl)butane,
3-(1-caprolactamyl)-1-(tetrahydro-1,4-oxazin-3-on-1-yl)butane,
1-(oxazolidin-4-on-3-yl)-3-(1-piperidonyl)butane,
3-(oxazolidin-4-on-3-yl)-1-(1-piperidonyl)butane,
1-(oxazolidin-4-on-3-yl)-3-(1-pyrrolidonyl)butane,
3-(oxazolidin-4-on-3-yl)-1-(1-pyrrolidonyl)butane,
1-(oxazolidin-4-on-3-yl)-3-(tetrahydro-1,4-oxazin-13-on-1-yl)butane,
3-(oxazolidin-4-on-3-yl)-1-(tetrahydro-1,4-oxazin-3-on-1-yl)butane,
1-(1-piperidonyl)-3-(1-pyrrolidonyl)butane,
3-(1-piperidonyl)-1-(1-pyrrolidonyl)butane,
1-(1-piperidonyl)-3-(tetrahydro-1,4-oxazin-3-on-1-yl)butane,
3-(1-piperidonyl)-1-(tetrahydro-1,4-oxazin-3-on-1-yl)butane,
1-(1-pyrrolidonyl)-3-(tetrahydro-1,4-oxazin-3-on-1-yl)butane, and
3-(1-pyrrolidonyl)-1-(tetrahydro-1,4-oxazin-3-on-1-yl)butane.

9. A pharmaceutical composition comprising at least one compound as claimed in claim 5 and at least one pharmaceutically active ingredient.

10. A cosmetic composition comprising at least one compound as claimed in claim 5 and at least one cosmetically active ingredient.

* * * * *

UNITED STATES PATENT AND TRADEMARK OFFICE
CERTIFICATE OF CORRECTION

PATENT NO. : 6,497,886 B1
DATED : December 24, 2002
INVENTOR(S) : Breitenbach et al.

It is certified that error appears in the above-identified patent and that said Letters Patent is hereby corrected as shown below:

Column 15,
Line 28, "ϵ-ca-prolactam" should be -- ϵ-caprolactam --.

Column 16,
Line 45, "oxazin-13-" should read -- oxaxin-3- --.

Signed and Sealed this

Twelfth Day of August, 2003

JAMES E. ROGAN
*Director of the United States Patent and Trademark Office*